United States Patent
Kim et al.

(10) Patent No.: US 10,859,498 B2
(45) Date of Patent: Dec. 8, 2020

(54) METHOD FOR VISUALIZATION OF CONJUNCTIVAL CELLS USING FLUOROQUINOLONE ANTIBIOTICS AND METHOD FOR DIAGNOSIS OF OCULAR LESIONS USING THE SAME

(71) Applicant: POSTECH ACADEMY-INDUSTRY FOUNDATION, Pohang-si (KR)

(72) Inventors: Seonghan Kim, Seoul (KR); Ki Hean Kim, Pohang-si (KR); Myoung Joon Kim, Seoul (KR); Seunghun Lee, Daegu (KR); Hoon Cheol Jang, Seoul (KR); Viet Hoan Le, Pohang-si (KR); Soo Hyun Park, Sejong-si (KR)

(73) Assignee: Postech Academy-Industry Foundation, Pohang-si (KR)

( * ) Notice: Subject to any disclaimer, the term of this patent is extended or adjusted under 35 U.S.C. 154(b) by 0 days.

(21) Appl. No.: 16/289,536

(22) Filed: Feb. 28, 2019

(65) Prior Publication Data

US 2020/0278299 A1   Sep. 3, 2020

(51) Int. Cl.
*G01N 21/64* (2006.01)
*G01N 33/58* (2006.01)
*G01N 33/50* (2006.01)

(52) U.S. Cl.
CPC ..... *G01N 21/6458* (2013.01); *G01N 21/6447* (2013.01); *G01N 21/6486* (2013.01);
(Continued)

(58) Field of Classification Search
CPC ........... G01N 21/6458; G01N 21/6447; G01N 21/6486
See application file for complete search history.

(56) References Cited

U.S. PATENT DOCUMENTS

2013/0149734 A1* 6/2013 Ammar ............ G01N 21/6408
435/29

FOREIGN PATENT DOCUMENTS

KR   10-1662775   10/2016

OTHER PUBLICATIONS

Lee et al., (In vivo 3D measurement of moxifloxacin and gatifloxacin distributions in the mouse cornea using multiphoton microscopy, Published in: Scientific Reports, 6, 25339, Electronic Pub. Date; May 3, 2016, Digital Object Identifier: 10.1038/srep25339, ISSN: 2045-2322) (Year: 2016).*

(Continued)

*Primary Examiner* — Hugh Maupin
(74) *Attorney, Agent, or Firm* — Morgan, Lewis & Bockius LLP

(57) ABSTRACT

A method for visualization of conjunctival cells using fluoroquinolone antibiotics and a method for diagnosis of ocular lesions using the same. The method for visualization of conjunctival cells using fluoroquinolone antibiotics includes staining goblet cells of ocular conjunctiva with moxifloxacin, which is a fluoroquinolone antibiotic, and exciting the stained goblet cells with single photons in the near-UV region or in the visible region, followed by fluorescence photographing of the goblet cells, thereby enabling acquisition of morphological information on living tissue without damage to or destruction of the ocular conjunctiva. Specifically, the method for visualization of conjunctival cells includes: a conjunctiva staining step in which ocular conjunctiva is stained with a fluoroquinolone antibiotic; a light irradiation step in which the ocular conjunctiva stained with the fluoroquinolone antibiotic is irradiated with light from a light source; and a conjunctiva photographing step in which the ocular conjunctiva is photographed using an image pickup unit through the fluoroquinolone antibiotic fluores- (Continued)

cence-excited by light in the light irradiation step, wherein, in the conjunctiva staining step, goblet cells of the ocular conjunctiva are stained with the fluoroquinolone antibiotic; in the light irradiation step, the light source emits single photons; and, in the conjunctiva photographing step, the image pickup unit photographing the ocular conjunctiva is a high-magnification fluorescence microscope or a slit lamp microscope.

9 Claims, 6 Drawing Sheets

(52) U.S. Cl.
CPC ....... *G01N 33/5091* (2013.01); *G01N 33/582* (2013.01); *G01N 2021/6439* (2013.01); *G01N 2800/162* (2013.01)

(56) References Cited

OTHER PUBLICATIONS

Hyun-Yi et al. (In vitro ultraviolet-induced damage in human corneal, lens, and retinal pigment epithelial cells, Published in: Molecular Vision, 17, 237-246 Electronic Publication Date: Jan. 21, 2011, ISSN: 1090-0535) (Year: 2011).*

* cited by examiner (a)

(b)

METHOD FOR VISUALIZATION OF CONJUNCTIVAL CELLS USING FLUOROQUINOLONE ANTIBIOTICS AND METHOD FOR DIAGNOSIS OF OCULAR LESIONS USING THE SAME

STATEMENT REGARDING RESEARCH

The research related to this disclosure was supported by the projects listed below:
[Project number] 1415158923
[Ministry] Ministry of Trade, Industry and Energy
[Management agency] Korea Evaluation Institute of Industrial Technology
[Program name] The Industrial Technology Innovation Program (No. 10048358) funded by the Ministry of Trade, Industry & Energy of the Korean Government
[Project name] Development of robotic core technologies for patient-specific precision examination and keratoplasty based on fabrication of 50 µm-level layered artificial cornea
[Contribution ratio] 20%
[Supervision institution] POSTECH Research and Business Development Foundation
[Period] Jul. 1, 2018~Jun. 30, 2019
[Project number] 1711068372
[Ministry] Ministry of Science and ICT
[Management Agency] National Research Foundation of Korea
[Program name] Korea-Sweden Research Cooperation Program (2017R1A2A1A18070960) of the National Research Foundation (NRF) funded by the Korean Government (MEST)
[Project name] In vivo screening of apatamers for diabetes treatment
[Contribution ratio] 40%
[Supervision institution] POSTECH Research and Business Development Foundation
[Period] Mar. 1, 2018~Feb. 28, 2019
[Project number] 1711070054
[Ministry] Ministry of Science and ICT
[Management Agency] National Research Foundation of Korea
[Program name] The Brain Research Program through the National Research Foundation of Korea (NRF) funded by the Ministry of Science, ICT & Future Planning (NRF-2017M3C7A 1044964)
[Project name] Development of high-speed 3D fluorescence microscope systems for comprehensive molecular imaging of optical cleared mouse brains
[Contribution ratio] 40%
[Supervision institution] POSTECH Research and Business Development Foundation
[Period] Mar. 1, 2018~Dec. 31, 2018

FIELD

The present invention relates to a method for visualization of conjunctival cells using fluoroquinolone antibiotics and a method for diagnosis of ocular lesions using the same. More particularly, the present invention relates to a method for visualization of conjunctival cells using fluoroquinolone antibiotics, which includes staining goblet cells of ocular conjunctiva with moxifloxacin, which is a fluoroquinolone antibiotic, and exciting the stained goblet cells with single photons in the near-UV region or in the visible region, followed by fluorescence photographing of the goblet cells, thereby enabling acquisition of morphological information on living tissue without damage to or destruction of the ocular conjunctiva, and a method for diagnosis of ocular lesions using the same.

BACKGROUND

Optical microscopy capable of high-resolution photographing of cells in living tissue is used in biological research and for clinical diagnosis in ophthalmology and dermatology.

In clinical diagnosis, non-invasive optical microscopy, which mainly utilizes reflection of light, is used, and an example of the non-invasive optical microscopy includes confocal reflectance microscopy. However, an image of cells of living tissue obtained by the confocal reflectance microscopy has a low contrast. Accordingly, when there is a need for enhancement of image contrast, fluorescence microscopy, in which living tissue is stained with a fluorescent material (a fluorescent probe), followed by excitation fluorescence photographing of the living tissue, is used.

Here, the fluorescent material allows emission of strong fluorescence signals from a specific region of interest, thereby enabling high-contrast and high-speed imaging.

Although various fluorescent materials are used for animal subjects, indocyanine green and fluorescein are used for the human body as a fluorescent material for staining of blood vessels.

Since staining of blood vessels alone is not enough to diagnose lesions or cancer, or to obtain morphological information on cells, staining of cells in the human body is necessary for accurate diagnosis.

For this purpose, although various studies have been made to develop fluorescent medicines for staining of human cells, a fluorescent material applicable to the human body has not been yet developed in the art due to toxicity to cells and the like.

Among non-toxic medicines that can be used to stain human cells, moxifloxacin is an antibacterial agent used to treat or prevent bacterial infections in clinical practice and has properties suitable for staining of living tissue and fluorescence imaging, such as intrinsic fluorescence and high penetrability to living tissue.

However, since excitation efficiency of moxifloxacin reaches maximum at 280 nm in the mid-UV region, which is harmful to the human body, it is difficult to use moxifloxacin in in-vivo photographing of the human body.

In order to resolve such a problem, recently, fluorescence imaging based on two-photon excitation of moxifloxacin at a near-infrared excitation wavelength has been demonstrated and it was confirmed that human tissue and cells can be stained with moxifloxacin, thereby enabling acquisition of a high resolution image thereof.

The conjunctiva of the eye is a thin, transparent mucosa covering the inside of the eyelid and a white part (sclera) of the eye. The conjunctiva is located on the outermost surface of the eye along with the cornea to protect the eye. In addition, the conjunctiva consists of a surface cell layer composed of epithelial cells and goblet cells and underlying stroma, in which the goblet cells secrete mucus, a component of tears and the stroma is rich in blood vessels and lymphoid tissues and has immune-related cells distributed throughout.

If there is abnormal mucus secretion from the goblet cells, which produce mucus, a component of tears, dry eye syndrome and subsequent inflammation can occur. Abnormal mucus secretion from the goblet cells is caused by changes in density of the goblet cells in the conjunctiva or by morphological changes of the goblet cells, and diseases accompanied by reduction in the number of goblet cells are known clinically.

Therefore, technologies for imaging goblet cells can provide information useful for diagnosis of eye diseases and severity thereof and for evaluation of treatment response and clinical observation of progression of the diseases.

Among these technologies, currently, impression cytology is used for determination of the density of the goblet cells in the conjunctiva. Impression cytology is a method in which a filter paper is pressed against the corneal limbus to extract an uppermost cell layer of the conjunctiva, which in turn is stained, followed by photographing thereof, and is thus easy and simple to operate. However, this method is likely to cause slight damage to the conjunctiva and is not recommended for multiple examinations.

Recently, as an alternative to impression cytology, an examination method of calculating the density of the goblet cells through noninvasive photographing of conjunctival cells by confocal reflectance microscopy.

In confocal reflectance microscopy images, the goblet cells are relatively high in reflectivity, appear large and round, and thus are distinguished from surrounding epithelial cells. However, confocal reflectance microscopy is not widely used due to problems of low contrast, high equipment expense, and difficulty in operation due to the need to place an objective lens of a microscope close to the eyeball.

PRIOR LITERATURE (Patent document 0001) Korean Patent Publication No. 10-2016-0063174 (Title of the Invention: APPARATUS FOR DIAGNOSING DRY EYE SYNDROME AND METHOD FOR DIAGNOSING DRY EYE SYNDROME USING THE SAME, Publication date: Jun. 3, 2016)

SUMMARY

It is an aspect of the present invention to provide a method for visualization of conjunctival cells using fluoroquinolone antibiotics, which includes staining goblet cells of ocular conjunctiva with moxifloxacin, which is a fluoroquinolone antibiotic, and exciting the goblet cells with single photons in the near UV region or in the visible region, followed by fluorescence photographing of the goblet cells, thereby enabling acquisition of morphological information on living tissue without damage to or destruction of the ocular conjunctiva, and a method for diagnosis of ocular lesions using the same.

In accordance with one aspect of the present invention, there is provided a method for visualization of conjunctival cells using a fluoroquinolone antibiotic, including: a conjunctiva staining step in which the ocular conjunctiva is stained with the fluoroquinolone antibiotic; a light irradiation step in which the ocular conjunctiva stained with the fluoroquinolone antibiotic is irradiated with light from a light source; and a conjunctiva photographing step in which the ocular conjunctiva is photographed using an image pickup unit through the fluoroquinolone antibiotic fluorescence-excited by light in the light irradiation step, wherein, in the conjunctiva staining step, goblet cells of the ocular conjunctiva are stained with the fluoroquinolone antibiotic; in the light irradiation step, the light source emits single photons and continuous wave light emitted from the light source has a wavelength band within the near UV and visible regions; and in the conjunctiva photographing step, the image pickup unit photographing the ocular conjunctiva is a high-magnification fluorescence microscope (a macroscope) or a slit lamp microscope.

In the conjunctiva staining step, the fluoroquinolone antibiotic used to stain the ocular conjunctiva may include moxifloxacin.

In the light irradiation step, continuous wave light emitted from the light source has a wavelength band within the near-UV and visible regions.

The wavelength band within the near UV and visible regions may range from 300 nm to 476 nm.

In accordance with another aspect of the present invention, there is provided a method for diagnosis of ocular lesions using an image of goblet cells of ocular conjunctiva obtained by the method for visualization of conjunctival cells using the fluoroquinolone antibiotic according to the present invention, wherein diagnosis of the ocular lesions is conducted based on change in the number or area of goblet cells per unit area.

The ocular lesions may include chemical burns, keratoconjunctivitis, ocular cicatricial pemphigoid, Stevens-Johnson syndrome, and superior limbic keratoconjunctivitis.

The method for visualization of conjunctival cells using fluoroquinolone antibiotics and the method for diagnosis of ocular lesions using the same according to the present invention have the following effects:

First, since the ocular conjunctiva is stained with moxifloxacin, followed by irradiation of moxifloxacin with light in the visible region, high-speed direct photographing of conjunctival cells is possible without damage to the ocular conjunctiva, thereby allowing quick and accurate diagnosis.

Second, through staining of the ocular conjunctiva with moxifloxacin, goblet cells of the ocular conjunctiva can be photographed using a high-magnification fluorescence microscope or a slit lamp microscope instead of an expensive high-performance microscope, such as a confocal fluorescence microscope, thereby allowing reduction in limitation on detection equipment.

Third, ocular lesions can be diagnosed based on numerical or morphological changes of goblet cells of the ocular conjunctiva.

DRAWINGS

Figure 5:
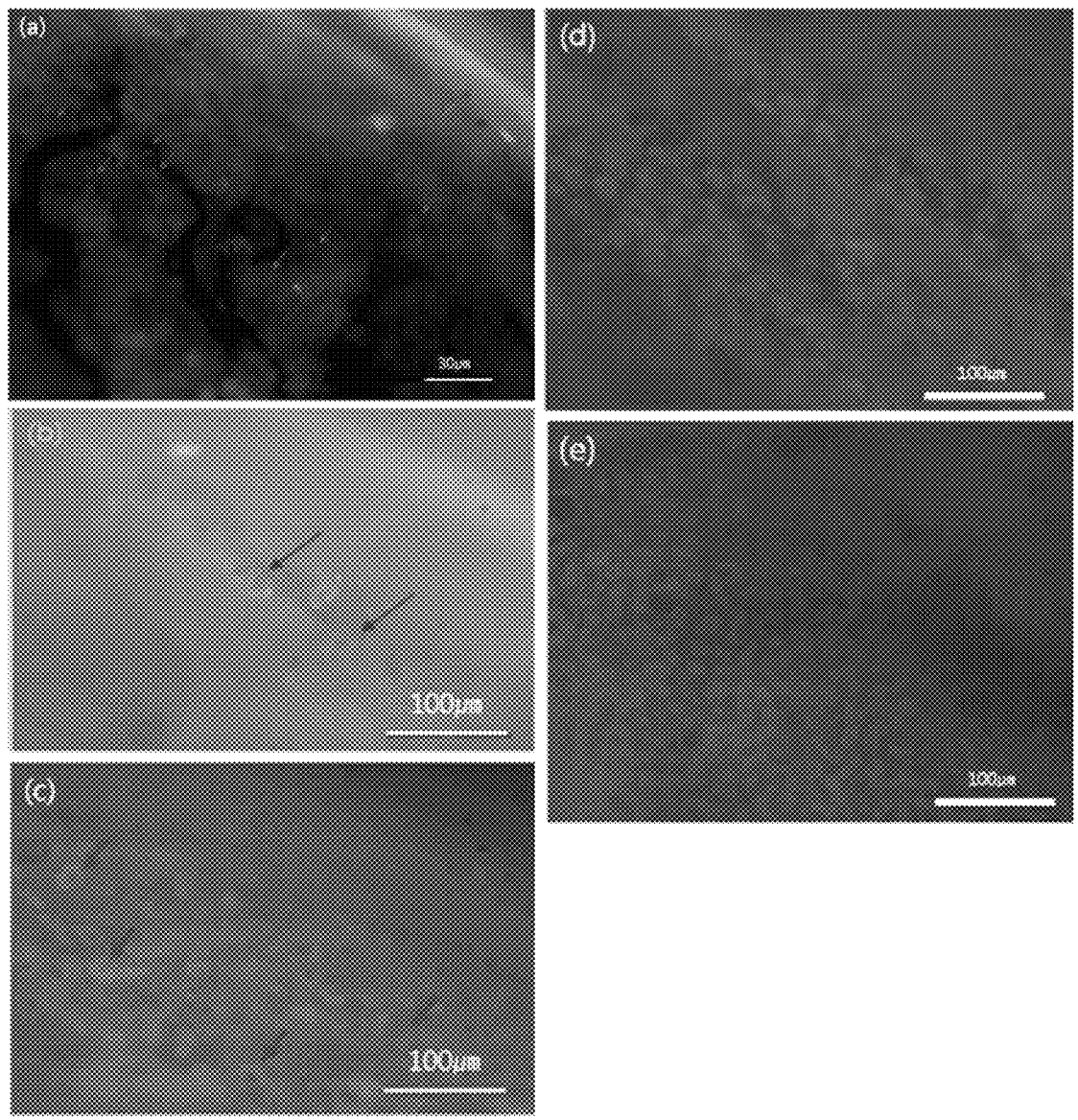

FIG. 5(a) to FIG. 5(e) are images of moxifloxacin-stained conjunctiva of a living rat, obtained by the method for visualization of conjunctival cells using fluoroquinolone antibiotics according to the present invention. FIG. 5(a) to FIG. 5(c) are high-magnification fluorescence microscopy images of moxifloxacin-stained bulbar conjunctiva of the rat, FIG. 5(d) is a high-magnification fluorescence microscopy image of moxifloxacin-stained conjunctiva of the rat, and FIG. 5(e) is a high-magnification fluorescence microscopy image of moxifloxacin-stained orbital or palpebral conjunctiva of the rat.

Figure 6:
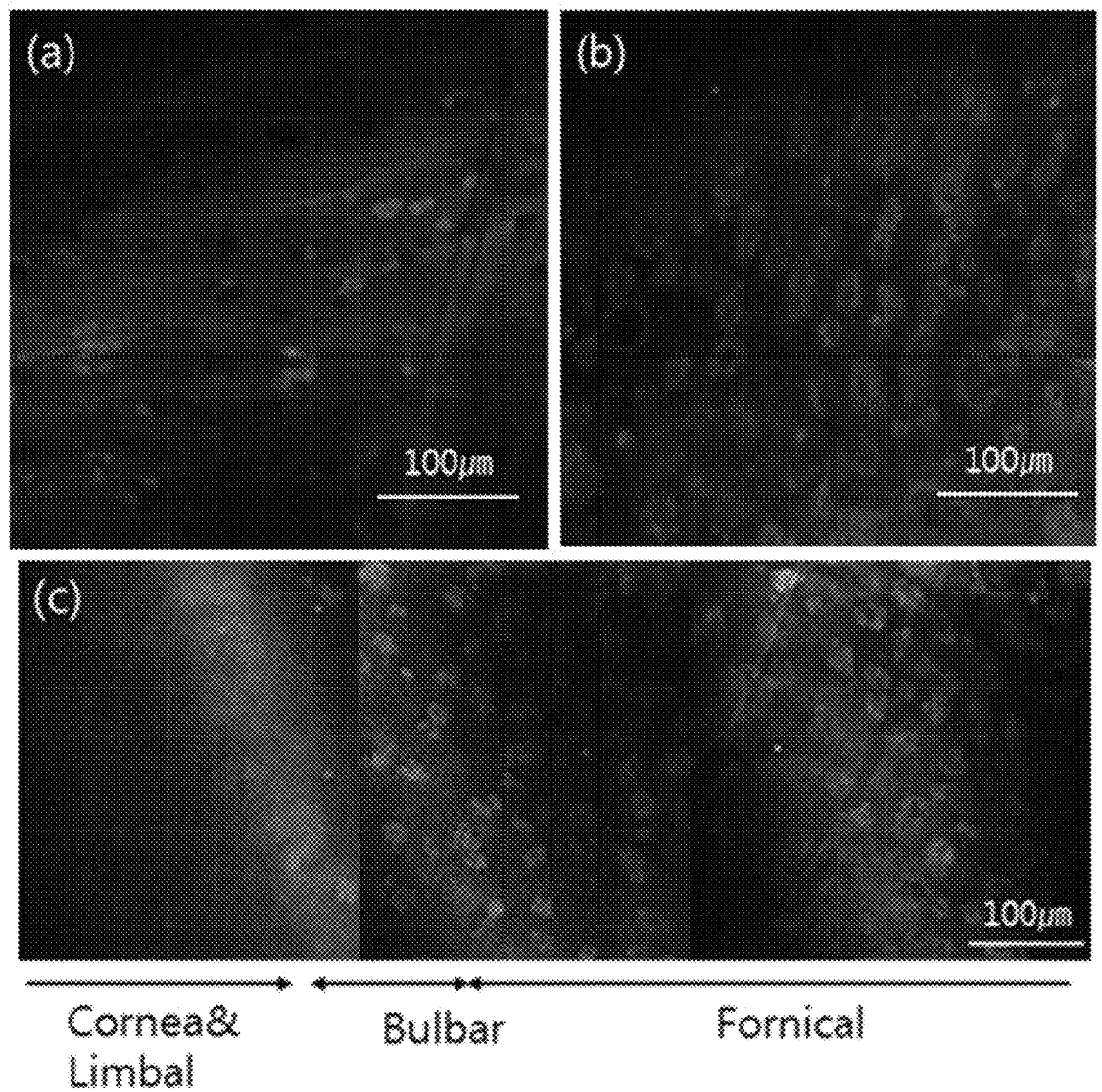

FIG. 6(a) to FIG. 6(c) are images of moxifloxacin-stained conjunctiva of a rat, obtained by the method for visualization of conjunctival cells using fluoroquinolone antibiotics according to the present invention. FIG. 6(a) is a confocal fluorescence microscopy image of moxifloxacin-stained bulbar conjunctiva of the rat, FIG. 6(b) is a confocal fluorescence microscopy image of moxifloxacin-stained fornix conjunctiva of the rat, and FIG. 6(c) is a continuation of respective confocal fluorescence microscopy images of the moxifloxacin-stained bulbar conjunctiva and fornix conjunctiva of the conjunctiva of the rat.

DETAILED DESCRIPTION

Hereinafter, embodiments of the present invention will be described with reference to the accompanying drawings. It should be noted that like components will be denoted by like reference numerals throughout the specification and the accompanying drawings. In addition, descriptions of details apparent to those skilled in the art will be omitted for clarity.

Now, a method for visualization of conjunctival cells using fluoroquinolone antibiotics according to the present invention will be described with reference to FIG. 1 to FIG. 6.

Figure 1:
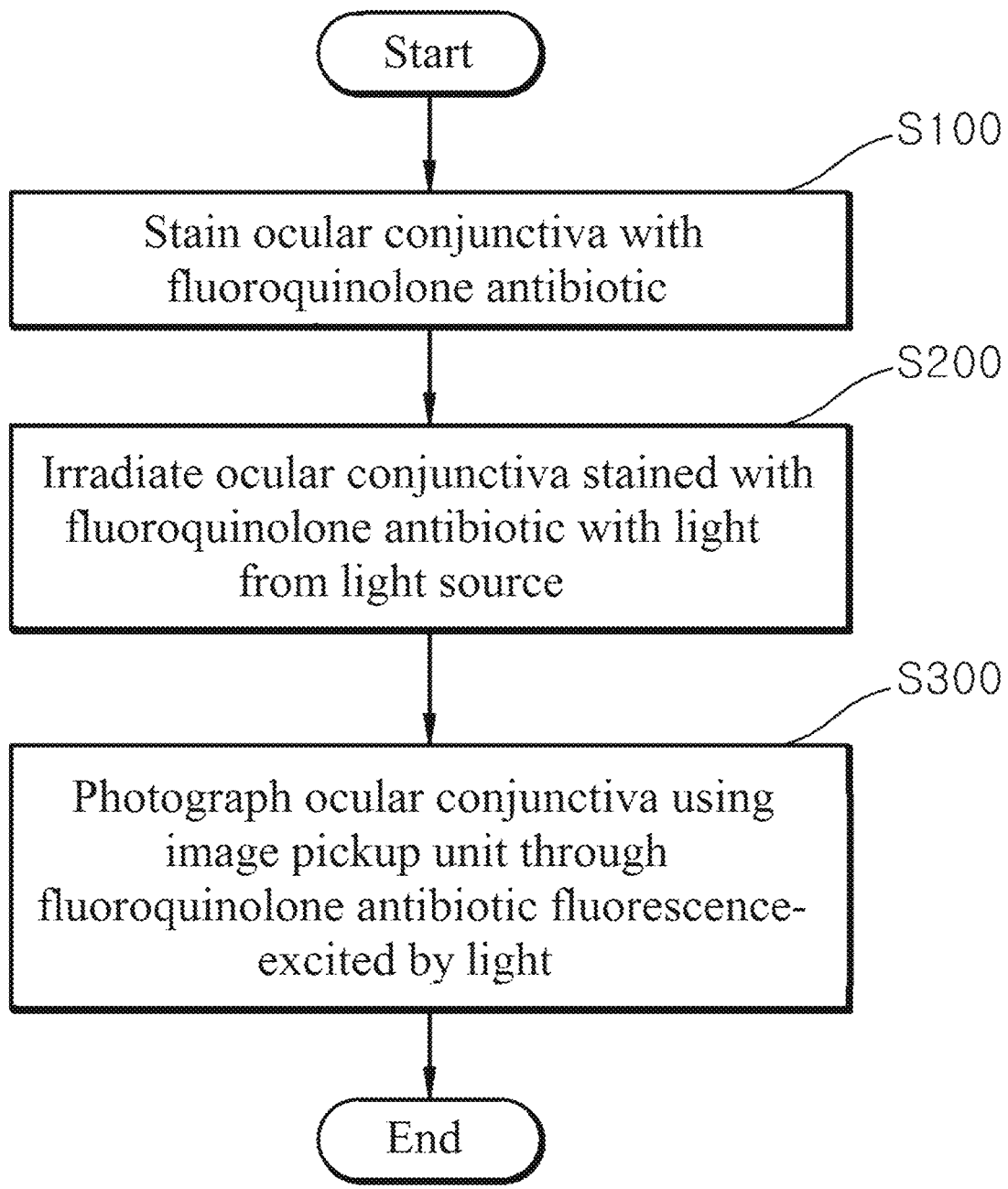
FIG. 1 is a flow diagram of a method for visualization of conjunctival cells using fluoroquinolone antibiotics according to the present invention.

Referring to FIG. 1, the method for visualization of conjunctival cells using fluoroquinolone antibiotics according to the present invention includes a conjunctiva staining step (S100), a light irradiation step (S200), and a conjunctiva photographing step (S300).

Prior to describing the method for visualization of conjunctival cells using fluoroquinolone antibiotics according to the present invention, a mechanism of single-photon excitation will be described with reference to FIG. 2.

Figure 2:
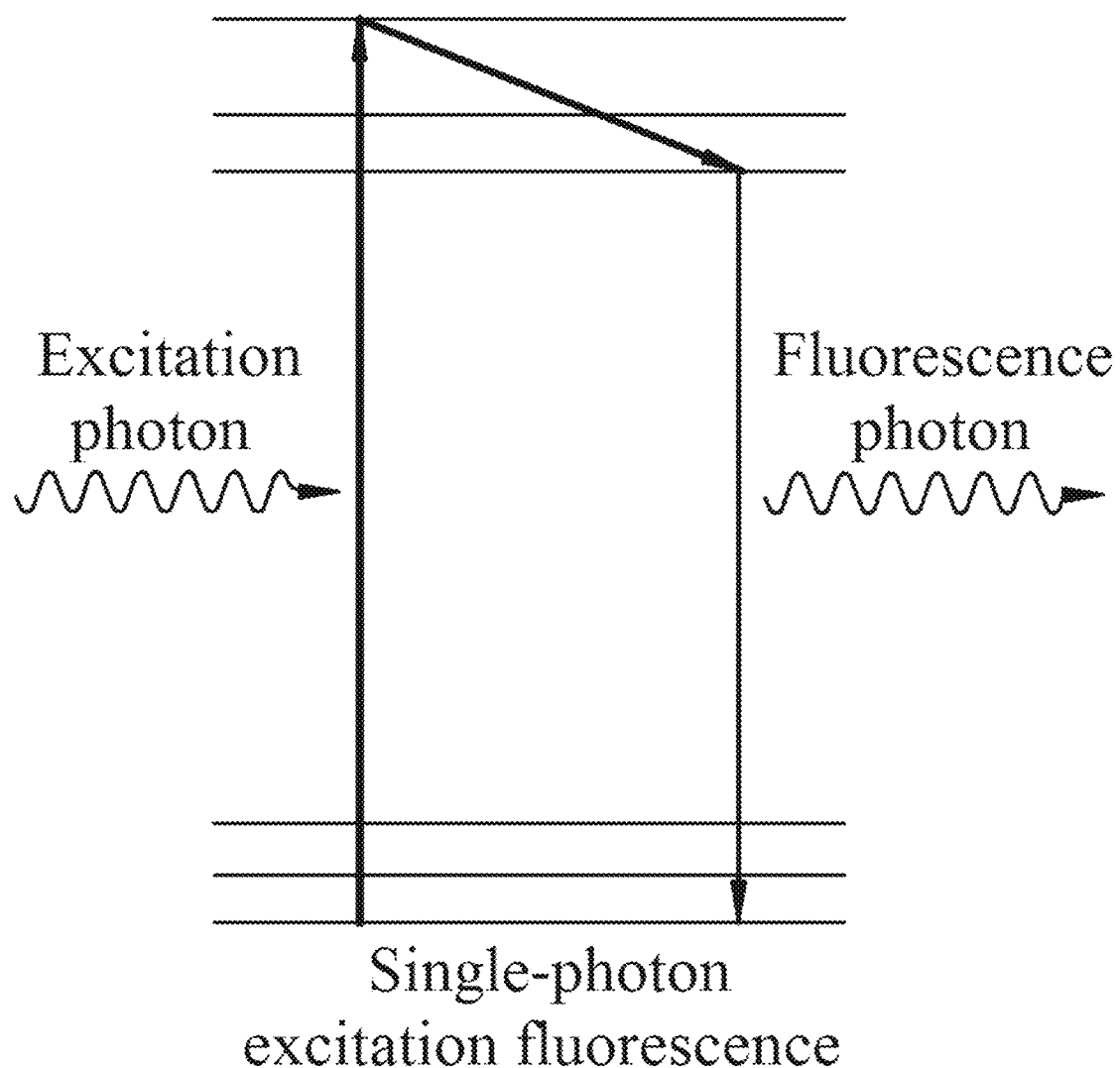
FIG. 2 is a diagram illustrating a mechanism of single-photon excitation used in the method for visualization of conjunctival cells using fluoroquinolone antibiotics.

Referring to FIG. 2, the energy level of an electron in a molecule of a fluorescent material is raised to an excited state from a ground state by an excitation photon.

Then, the electron relaxes to the ground state by emitting a fluorescence photon. Here, the electron absorbs one excitation photon and emits one fluorescence photon, a phenomenon called single-photon excitation fluorescence. Due to single-photon excitation fluorescence, single-photon excitation efficiency is higher than two-photon excitation efficiency, whereby fluorescence imaging is possible even when the luminous intensity of a light source described below is reduced.

That is, molecular activities in living cells or tissue can be observed at high resolution by optical fluorescence microscopy by treating the cells or tissue with a fluorescent material. This is because an electron in the fluorescent material emits a fluorescence photon having a unique color in the process of being excited by an excitation photon and returning to the original state thereof.

When such a fluorescent material is injected into living tissue and is absorbed by cells of the living tissue to be maintained at a high concentration, high-contrast photographing of the living tissue is possible through fluorescence of the fluorescent material.

That is, morphological information on living tissue can be obtained through staining of the living tissue with a fluorescent material, provided that the fluorescent material is not toxic to the human body and can be fluorescence-excited by light in the visible region, which is harmless to the human body.

Examples of the fluoroquinolone antibiotics used to stain living tissue may include moxifloxacin, gatifloxacin, pefloxacin, difloxacin, nofloxacin, ciprofloxacin, ofloxacin, and enrofloxacin. Thereamong, moxifloxacin capable of exhibiting autofluorescence in the visible region is used to stain living tissue, herein.

Figure 3:
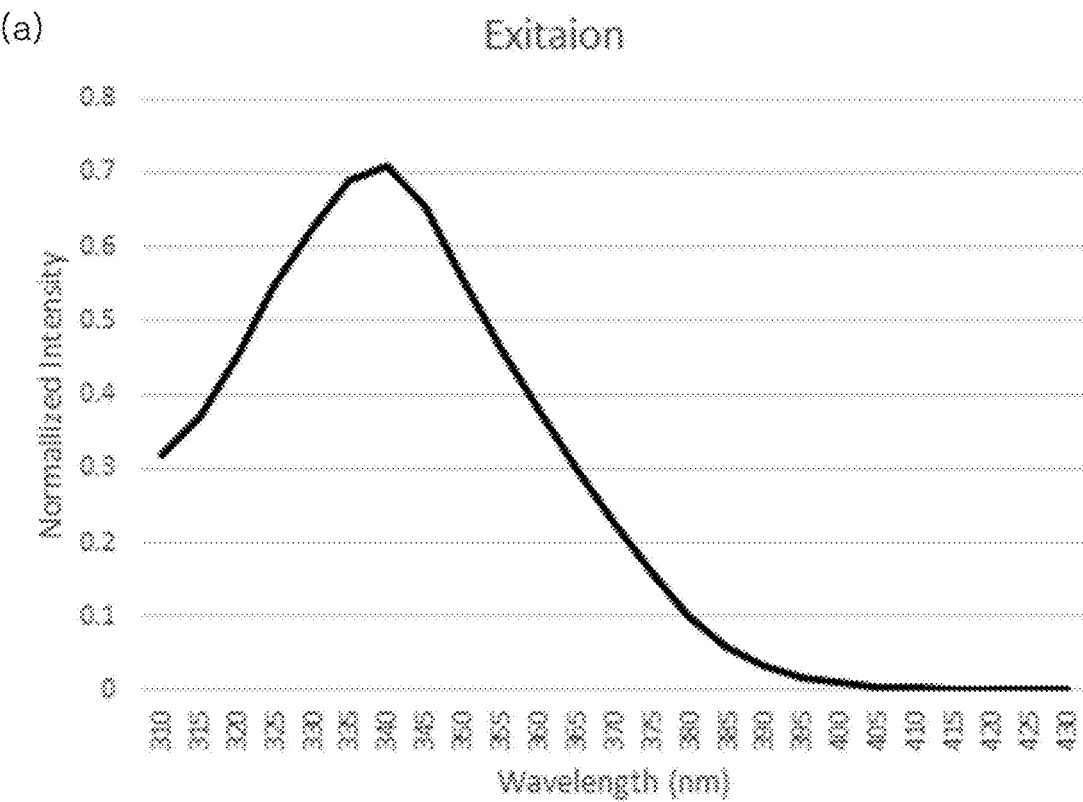
FIG. 3 shows a single-photon excitation spectrum and fluorescence emission spectrum in the near UV region and visible regions of moxifloxacin used in the method for visualization of conjunctival cells using fluoroquinolone antibiotics.
Figure 3:
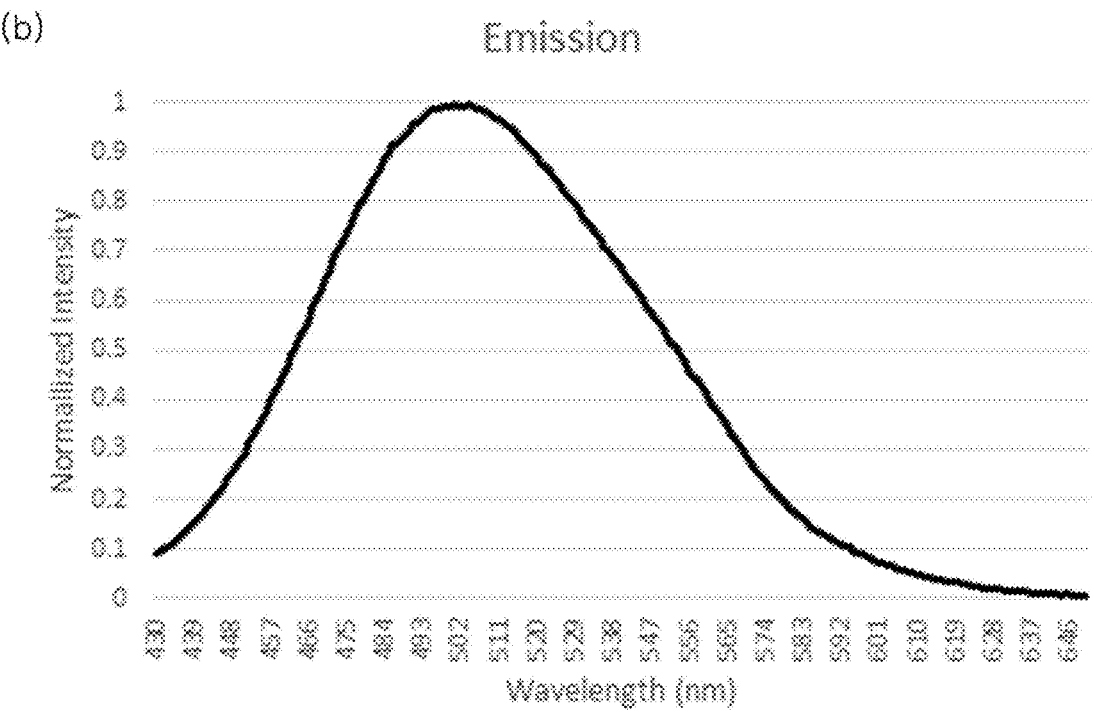
Figure 4:
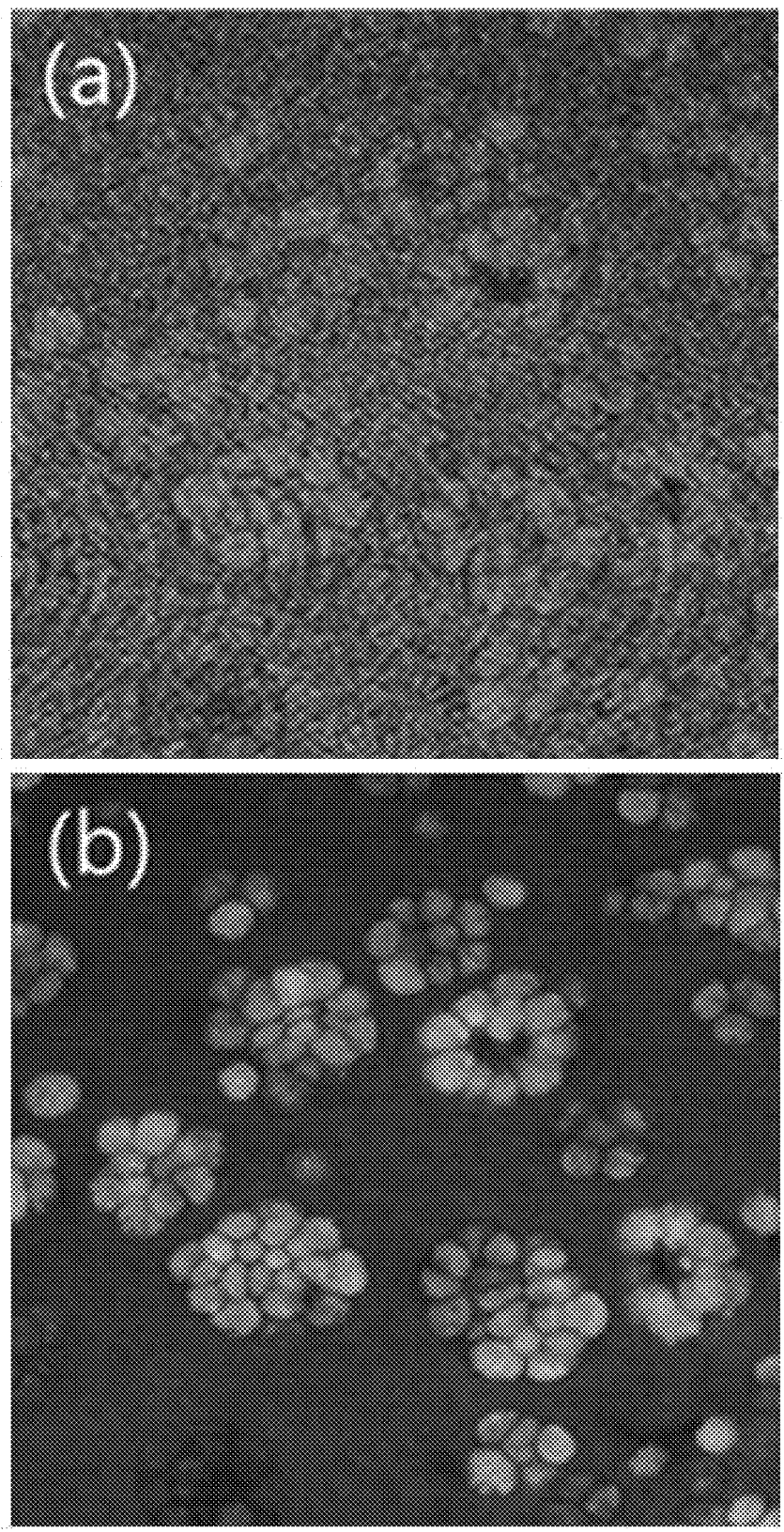
FIG. 4(a) is a reflectance confocal microscopy image of ocular conjunctiva of a mouse before staining of the ocular conjunctiva with moxifloxacin and FIG. 4(b) is a confocal fluorescence microscopy image of the ocular conjunctiva of the mouse after staining of the ocular conjunctiva with moxifloxacin.

Next, a single-photon excitation spectrum and fluorescence emission spectrum in the near UV and visible regions of moxifloxacin used in the method for visualization of conjunctival cells using fluoroquinolone antibiotics according to the present invention will be described with reference to FIG. 3.

FIG. 3(a) and FIG. 3(b) show an excitation spectrum and fluorescence emission spectrum in the near UV and visible regions of moxifloxacin, respectively.

As moxifloxacin used in the method for visualization of conjunctival cells using fluoroquinolone antibiotics according to the present invention, Vigamox eye drop 0.5% commercially available from Alcon Lab Inc. (USA) was used.

As shown in FIG. 3(a) and FIG. 3(b), excitation efficiency of moxifloxacin had a maximum value at around 340 nm in the near UV region and then gradually decreased with increasing wavelength.

However, it was confirmed that excitation of moxifloxacin was also possible at a wavelength of 405 nm to 478 nm, which falls within the visible region outside the near UV region. Particularly, the fluorescence intensity at 405 nm was about 0.5% of that at 340 nm and was much higher than two-photon fluorescence intensity based on 700 nm excitation light.

Accordingly, in the method for visualization of conjunctival cells according to the present invention, a continuous wave light source emitting light in a wavelength band of 300 nm to 476 nm is used, such that imaging speed can be improved by increasing the intensity of fluorescence signals using light in the mid- to near-UV regions, while applicability to living tissue can be improved using light in the visible region.

In the aforementioned single-photon wavelength band, wavelengths falling within the near UV region can cause damage to cells of living tissue. However, based on the fact that single-photon excitation efficiency is high, these wavelengths can also be used for photographing of living tissue by reducing luminous intensity of a light source.

Next, the method for visualization of conjunctival cells using fluoroquinolone antibiotics according to the present invention will be described in detail with reference to FIG. 1.

In the conjunctiva staining step S100, cells of ocular conjunctiva, living tissue to be tested, are stained with a fluoroquinolone antibiotic. Herein, as the fluoroquinolone antibiotic, moxifloxacin, which is a fluoroquinolone antibiotic, is used.

In the conjunctiva staining step S100, goblet cells of the ocular conjunctiva are stained with moxifloxacin.

In the light irradiation step S200, the ocular conjunctiva stained with moxifloxacin is irradiated with light from a light source. Here, the light source emits single photons, which are excitation light inducing fluorescence of the fluoroquinolone antibiotic, specifically, continuous wave light having the aforementioned wavelength band in the near UV and visible regions. In experimental examples described below, the light source emits continuous wave light having the aforementioned wavelength band in the near UV and visible regions to perform fluorescence excitation.

In the conjunctiva photographing step S300, photographing of the goblet cells is conducted using an image pickup unit through moxifloxacin which is fluorescence-excited by light in the light irradiation step S200, wherein the image pickup unit includes a high-magnification fluorescence microscope or a slit lamp microscope.

Next, the method for visualization of conjunctival cells using fluoroquinolone antibiotics according to the present invention will be described in more detail with reference to experimental examples.

Experimental Example 1: Photographing of Ocular Conjunctiva of Mouse with or without Moxifloxacin Staining FIG. 4(a) is a reflectance confocal microscopy image of ocular conjunctiva of a mouse before spray of moxifloxacin and FIG. 4(b) is a confocal fluorescence microscopy image of the ocular conjunctiva after spray of moxifloxacin.

Referring to FIG. 4(a) and FIG. 4(b), it can be seen that, before spray of moxifloxacin, photographing of goblet cells of the ocular conjunctiva was difficult due to nonspecific reflection of the cells and thus low imaging contrast, whereas, after spray of moxifloxacin, high-contrast photographing of the goblet cells of the ocular conjunctiva was possible due to single-photon excitation fluorescence of moxifloxacin staining the goblet cells.

That is, it was confirmed that a high concentration of moxifloxacin present in the goblet cells exhibited strong fluorescence, thereby enabling acquisition of higher-contrast morphological information than reflectance image information.

Experimental Example 2: Photographing of Ocular Conjunctiva of Rat Using High-Magnification Fluorescence Microscope FIG. 5(a) to FIG. 5(e) are images of moxifloxacin-stained conjunctiva of a living rat, obtained by the method for visualization of conjunctival cells using fluoroquinolone antibiotics according to the present invention.

Here, FIG. 5(a) to FIG. 5(c) are high-magnification fluorescence microscopy images of moxifloxacin-stained bulbar conjunctiva of the rat. Referring to FIG. 5(a) to FIG. 5(c), it can be seen that, in the bulbar conjunctiva, the distribution of goblet cells is sparse and the size of clusters of the goblet cells is small.

FIG. 5(d) is a high-magnification fluorescence microscopy image of moxifloxacin-stained fornix conjunctiva of the rat. Referring to FIG. 5(d), it can be seen that, in the fornix conjunctiva, the distribution of goblet cells is dense and the size of clusters of the goblet cells is large.

FIG. 5(e) is an image of moxifloxacin-stained orbital or palpebral conjunctiva of the rat, obtained using a high-magnification fluorescence microscope as the image pickup unit according to the present invention. Referring to FIG. 5(e), it can be seen that, in the palpebral conjunctiva, the distribution of goblet cells is dense and the size of clusters of the goblet cells is large.

That is, as shown in FIG. 5(a) to FIG. 5(e), goblet cells of the ocular conjunctiva of a living rat can be photographed by staining the conjunctiva of the rat with moxifloxacin. In addition, through staining of the ocular conjunctiva with moxifloxacin, an image of the goblet cells can also be obtained using a high-magnification fluorescence microscope instead of a high-performance microscope such as a confocal fluorescence microscope.

Experimental Example 3: Photographing of Ocular Conjunctiva of Rat Using High-Magnification Fluorescence Microscope FIG. 6(a) to FIG. 6(c) are confocal fluorescence microscopy images of moxifloxacin-stained conjunctiva of a rat, obtained by the method for visualization of conjunctival cells using fluoroquinolone antibiotics according to the present invention.

In the method for visualization of conjunctival cells using fluoroquinolone antibiotics according to the present invention, the image pickup unit may further include a confocal fluorescence microscope.

FIG. 6(a) is a confocal fluorescence microscopy image of moxifloxacin-stained bulbar conjunctiva of the rat. Referring to FIG. 6(a), it can be seen that, in the bulbar conjunctiva, the distribution of goblet cells is sparse and the size of clusters of the goblet cells is small.

FIG. 6(b) is a confocal fluorescence microscopy image of moxifloxacin-stained fornix conjunctiva of the rat. Referring to FIG. 6(b), it can be seen that, in the fornix conjunctiva, the distribution of goblet cells is dense and the size of clusters of the goblet cells is large.

FIG. 6(c) is a continuation of respective confocal fluorescence microscopy images of the moxifloxacin-stained bulbar conjunctiva and fornix conjunctiva of the conjunctiva of the rat. Referring to FIG. 6(c), it can be seen that there are no goblet cells in the cornea and the limbus, goblet cells begin to appear in the bulbar conjunctiva, and, in a direction from the bulbar conjunctiva to the fornix conjunctiva, the distribution of goblet cells becomes denser and the size of colonies of the goblet cells becomes larger.

That is, as shown in FIGS. 6(a) to 6(c), goblet cells of the ocular conjunctiva of a living rat can be photographed by staining the conjunctiva of the rat with moxifloxacin.

Next, a method for diagnosis of ocular lesions according to the present invention will be described.

In the method for diagnosis of ocular lesions according to the present invention, diagnosis of the ocular lesions is performed using an image of goblet cells of the ocular conjunctiva, obtained by the method for visualization of conjunctival cells using fluoroquinolone antibiotics according to the present invention.

Diagnosis of the ocular lesions is conducted based on the number or area of goblet cells per unit area, wherein the ocular lesions may include chemical burns, keratoconjunctivitis, ocular cicatricial pemphigoid, Stevens-Johnson syndrome, and superior limbic keratoconjunctivitis. Table 1 shows diagnostic criteria for the ocular lesions.

TABLE 1

| | Loss in the number of bulbar conjunctiva goblet cells (%) | Loss of the number of palpebral conjunctiva goblet cells (%) | Difference (%) |
|---|---|---|---|
| Chemical burns | 60 | 40 | 20 |
| Keratoconjunctivitis sicca (KCS) | 70-80 | 60-80 | 10 |
| Ocular Cicatricial Pemphigoid (OCP) | 95 | 90-95 | 0-5 |
| Stevens-Johnson syndrome | 99-100 | 98-100 | 0-1 |
| Superior limbic keratoconjunctivitis (SLK) | 85 | 90 | −5 |

As shown in Table 1, chemical burns are diagnosed when 60% of the number of goblet cells of the bulbar conjunctiva is lost, 40% of the number of goblet cells of the palpebral conjunctiva is lost, and a difference in loss in the number of goblet cells between the bulbar conjunctiva and the palpebral conjunctiva is 20%.

Keratoconjunctivitis is diagnosed when 70% to 80% of the number of goblet cells of the bulbar conjunctiva is lost, 60% to 80% of the number of goblet cells of the palpebral conjunctiva is lost, and a difference in loss in the number of goblet cells between bulbar conjunctiva and palpebral conjunctiva is 0% to 10%.

Ocular cicatricial pemphigoid is diagnosed when 95% of the number of goblet cells of the bulbar conjunctiva is lost, 90% to 95% of the number of goblet cells of the palpebral conjunctiva is lost, and a difference in loss in the number of goblet cells between the bulbar conjunctiva and the palpebral conjunctiva is 0% to 5%.

Stevens-Johnson syndrome is diagnosed when 99% to 100% of the number of goblet cells of the bulbar conjunctiva is lost, 98% to 100% of the number of goblet cells of the palpebral conjunctiva is lost, and a difference in loss in the number of goblet cells between the bulbar conjunctiva and the palpebral conjunctiva is 0% to 1%.

Finally, superior limbic keratoconjunctivitis is diagnosed when 85% of the number of goblet cells of the bulbar conjunctiva is lost, 90% of the number of goblet cells of the palpebral conjunctiva is lost, and a difference in loss in the number of goblet cells between the bulbar conjunctiva and the palpebral conjunctiva is 5%.

Diagnosis of the ocular lesions set forth above may be carried out on the basis of change in the area of goblet cells per unit area, in addition to change in the number of goblet cells per unit area.

In addition, the method for visualization of conjunctival cells using fluoroquinolone antibiotics according to the present invention can provide morphological information on goblet cells for diagnosis of the ocular lesions, wherein the morphological information includes all kinds of morphological aspects, including the size and distribution of the goblet cells.

As described above, the method for visualization of conjunctival cells using fluoroquinolone antibiotics according to the present invention allows photographing of several conjunctival regions in the ocular conjunctiva, such that diagnosis of ocular lesions is conducted based on change in the number or area of goblet cells constituting the conjunctival regions.

Although some embodiments have been described herein, it should be understood that these embodiments are provided for illustration only and are not to be construed in any way as limiting the present invention, and that various modifications, changes, alterations, and equivalent embodiments can be made by those skilled in the art without departing from the spirit and scope of the invention.

What is claimed is:

1. A method for visualization of conjunctival cells using a fluoroquinolone antibiotic, comprising:
    a conjunctiva staining step in which ocular conjunctiva is stained with the fluoroquinolone antibiotic;
    a light irradiation step in which the ocular conjunctiva stained with the fluoroquinolone antibiotic is irradiated with light from a light source; and
    a conjunctiva photographing step in which the ocular conjunctiva is photographed using an image pickup unit through the fluoroquinolone antibiotic fluorescence-excited by light in the light irradiation step,
    wherein, in the conjunctiva staining step, goblet cells of the ocular conjunctiva are stained with the fluoroquinolone antibiotic,
    in the light irradiation step, the light source emits single photons and continuous wave light emitted from the light source has a wavelength band within the near UV and visible regions, and
    in the conjunctiva photographing step, the image pickup unit photographing the ocular conjunctiva is a high-magnification fluorescence microscope or a slit lamp microscope.

2. The method according to claim 1, wherein, in the conjunctiva staining step, the fluoroquinolone antibiotic used to stain the ocular conjunctiva comprises moxifloxacin.

3. A method for diagnosis of ocular lesions using an image of goblet cells of ocular conjunctiva obtained by the method according to claim 2, wherein diagnosis of the ocular lesions is conducted based on change in the number or area of the goblet cells per unit area.

4. The method according to claim 3, wherein the ocular lesions comprise chemical burns, keratoconjunctivitis, ocular cicatricial pemphigoid, Stevens-Johnson syndrome, and superior limbic keratoconjunctivitis.

5. The method according to claim 1, wherein the wavelength band within the near UV and visible regions ranges from 300 nm to 476 nm.

6. A method for diagnosis of ocular lesions using an image of goblet cells of ocular conjunctiva obtained by the method according to claim 5, wherein diagnosis of the ocular lesions is conducted based on change in the number or area of the goblet cells per unit area.

7. The method according to claim 6, wherein the ocular lesions comprise chemical burns, keratoconjunctivitis, ocular cicatricial pemphigoid, Stevens-Johnson syndrome, and superior limbic keratoconjunctivitis.

8. A method for diagnosis of ocular lesions using an image of goblet cells of ocular conjunctiva obtained by the method according to claim 1, wherein diagnosis of the ocular lesions is conducted based on change in the number or area of the goblet cells per unit area.

9. The method according to claim 8, wherein the ocular lesions comprise chemical burns, keratoconjunctivitis, ocular cicatricial pemphigoid, Stevens-Johnson syndrome, and superior limbic keratoconjunctivitis.

* * * * *